United States Patent
Winkler et al.

(10) Patent No.: US 6,524,103 B1
(45) Date of Patent: Feb. 25, 2003

(54) CARTRIDGE AND DENTAL APPLICATOR

(75) Inventors: Siegbert Winkler, Tisis (AT); Peter Kunkel, Triesen (LI); Franz Hohenegger, Vaduz (LI)

(73) Assignee: Ivoclar AG, Schaan (LI)

( * ) Notice: Subject to any disclaimer, the term of this patent is extended or adjusted under 35 U.S.C. 154(b) by 0 days.

(21) Appl. No.: 09/667,984

(22) Filed: Sep. 22, 2000

Related U.S. Application Data

(60) Provisional application No. 60/169,123, filed on Dec. 6, 1999.

(30) Foreign Application Priority Data

Sep. 23, 1999 (DE) .......................... 199 45 706

(51) Int. Cl.[7] .................................................. A61C 5/04
(52) U.S. Cl. ........................ 433/90; 604/310; 222/575
(58) Field of Search ............................. 433/90, 89, 80, 433/82; 604/310, 311, 218, 232, 235; 401/265; 222/386, 572, 575

(56) References Cited

U.S. PATENT DOCUMENTS

| | | | |
|---|---|---|---|
| 4,380,425 A | * 4/1983 | Edelman | 425/458 |
| 4,768,954 A | * 9/1988 | Dragan | 433/90 |
| 5,460,523 A | * 10/1995 | Schulman | 433/90 |
| 5,938,439 A | 8/1999 | Mertins | 433/90 |
| 6,238,212 B1 | * 5/2001 | Khachatoorian et al. | 433/89 |

* cited by examiner

Primary Examiner—John J. Wilson
Assistant Examiner—Melba Bumgarner
(74) Attorney, Agent, or Firm—John C. Thompson; Alan S. Korman

(57) ABSTRACT

A cartridge for receiving and dispensing a paste has a cartridge body having a front end with a lateral outlet opening for dispensing the paste material. The cartridge body has a longitudinal center axis and the outlet opening has a central axis inclined forwardly relatively to the longitudinal center axis. The outlet opening has a width measured in the direction perpendicular to the longitudinal center axis and an axial length measured in the direction of the longitudinal center axis. The width and the length are different, and the width is preferably greater than the axial length.

3 Claims, 2 Drawing Sheets

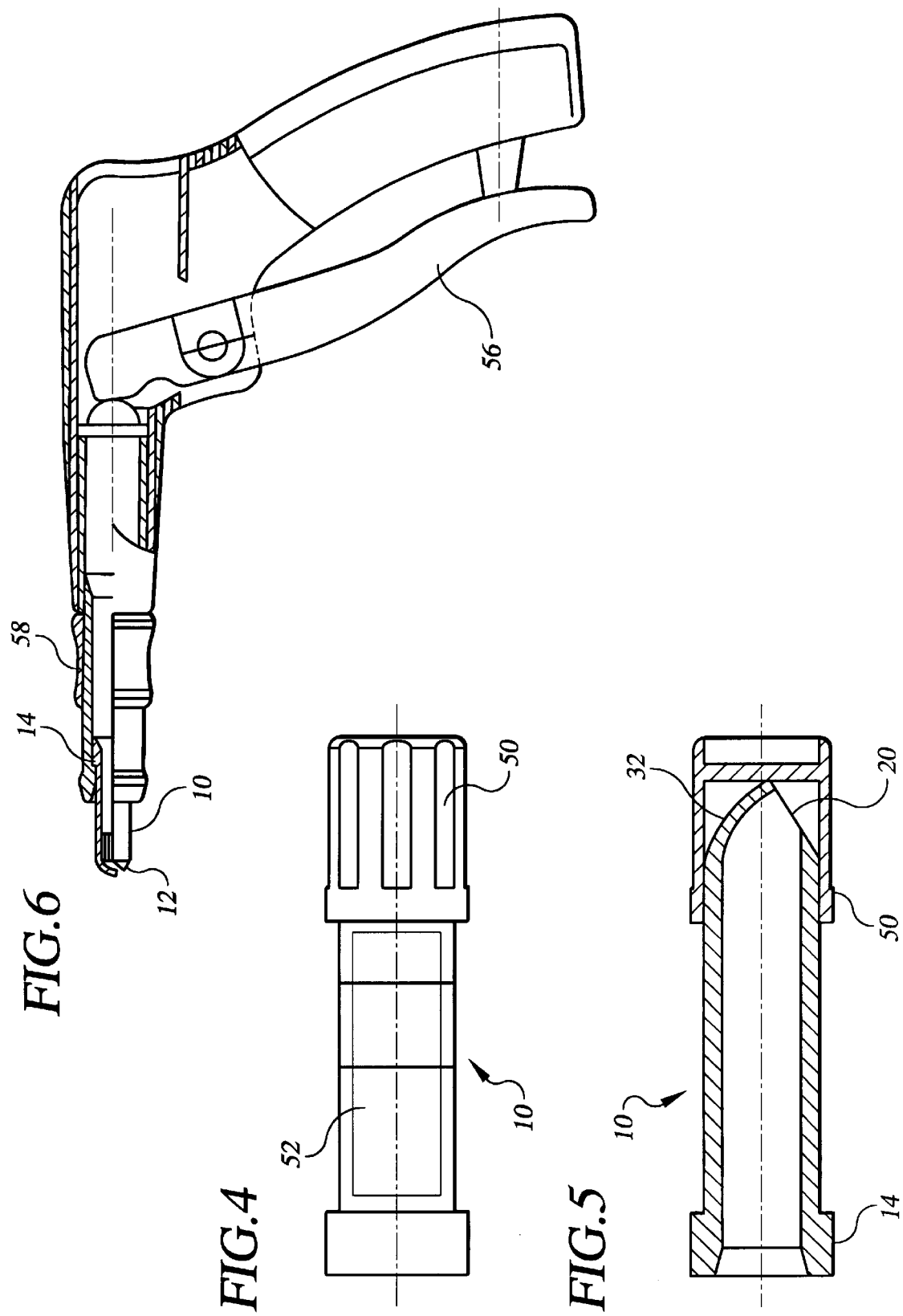

CARTRIDGE AND DENTAL APPLICATOR

CROSS-REFERENCE TO RELATED APPLICATIONS

This application claims foreign priority benefits under 35 U.S.C. §119(a)–(d) from German patent application ser. no P 199 45 706.9 filed Sep. 23, 1999. In addition, this application claims the benefit under 35 U.S.C. §119(e) of U.S. provisional patent application Ser. No. 60/169,123 filed Dec. 6, 1999.

BACKGROUND OF THE INVENTION

The present invention relates to a cartridge for receiving a paste-like material, especially a dental material, comprising a cartridge body having an outlet opening for dispensing the material, whereby the axis of the outlet opening extends laterally at a slant in the forward direction. The invention also relates to a dental applicator with an applicator body having an outlet opening at its forward portion and designed for dispensing a paste-like material, especially a dental material. The axis of the outlet opening extends at a slant laterally away from the applicator body.

Such a cartridge is, for example, disclosed in U.S. Pat. No. 5,938,439. The outlet opening of this cartridge is provided at the forward area of the cartridge whereby the dispensing device in this embodiment is a dispensing socket which extends laterally at a slant. The dispensing socket is comparatively long and has a comparatively limited cross-sectional area so that a corresponding flow resistance results for the dental material passing through the dispensing socket. However, in practice, this solution has been applied successfully when it is necessary to dispense low-viscosity dental materials which are completely dispensable when a dispensing plunger is introduced into the dispensing socket.

Furthermore, it has been suggested to provide a relatively short socket. This solution, with respect to flow-technological considerations, can be compared to the embodiment according to FIG. 2 of U.S. Pat. No 5,938,439. With it, it is possible to provide an only slightly reduced cross-sectional area for the dispensed dental material. Despite the relatively small reduction, the flow resistance however is relatively great, especially in devices in which a lateral deflection of viscous dental material is realized. In order to be able to deflect such viscous dental materials effectively to the side, it was long thought that substantial shearing forces must be overcome and the flow direction must be preadjusted to a certain flow length in order to produce again a flow that is approximately laminary after lowering the plunger.

Even though it is possible to design the dispensing socket in an arc shape with relatively large radius in the outward direction to thus provide favorable flow conditions, this would mean considerable material losses since the piston could not enter the right-angle curve of the dispensing socket as is conventional in the art.

Furthermore, there is often not enough space for such a curved embodiment. Therefore, various solutions with various compromises have been suggested in which the lateral projection extends only at a very small angle relative to the longitudinal axis of the cartridge body. The known solutions thus do not realize the desired considerable degree of lateral deflection of viscous dental materials despite the narrow design and the resulting easier maneuverability of the cartridge, especially of the cartridge tip.

It is therefore an object of the present invention to provide a cartridge for rather viscous materials as well as a dental applicator with which a considerable lateral deflection of the materials to be dispensed can be provided, even though the materials are highly viscous, without having to substantially increase the pressure forces. At the same time, however, a simple and inexpensive design of the cartridge or the dental applicator should be ensured.

SUMMARY OF THE INVENTION

This object is.inventively solved in that the outlet opening is provided in the forward end of the cartridge body itself and that the width of the outlet opening is especially different from the axial length of the outlet opening. In a preferred embodiment, the width of the outlet opening is greater than the axial length.

The object of the invention is also solved in that a dental applicator comprising an applicator body for receiving and dispensing a paste is provided that has a front end with an outlet opening for dispensing the paste material. The outlet opening has a width that is different from the axial length of the outlet opening; the width is especially greater than the length.

It is especially beneficial to provide the inventive outlet opening at the cartridge body itself. This, on the one hand, ensures that no laterally projecting protrusion impairs manipulation of the device so that filling of hard to reach cavities is not impaired. Surprisingly however, even rather deep cavities can be reached without problems. The lateral deflection angle of the dental material strand dispensed from the cartridge can be considerable, despite the minimal flow resistance, and can reach, for example, almost 90°. Experiments based on the present invention have shown that especially because of the increasing width, at least in portions of the cross-sectional area of the dental material strand dispensed from the outlet opening, the strand will bend rearwardly in a curved shape. Design variations of the deflection wall can be especially beneficial in this context.

It is especially advantageous that inventively the location of actual application, i.e., application of the strand of the material at the application location, is removed from the cartridge. The strand thus also serves simultaneously practically as a simulated dispensing socket. The stiffness and stability of the strand, aside from the effect of the high viscosity of the material, is affected substantially by two considerations. The asymmetric design of the outlet opening results in a relatively wide strand having flanks that act like ribs in a reinforcing way. Furthermore, the curvature that is imparted to the strand by the dispensing action gives the strand a somewhat improved stability. The curvature can be further enhanced by providing an inner radius or an inner curvature at the deflection wall which is positioned opposite the dispensing outlet opening.

It is understood that, aside from the preferred embodiment with a width of the outlet opening that widens from the rear to the front when viewed over the cartridge length, further suitable modified outlet openings can be realized. For example, by realizing a substantially diamond-shaped outlet opening a correspondingly shaped strand with a relatively high bending stiffness can be produced.

It is understood that the deformation resistance will increase when the strand geometry deviates to a greater extent from the circular cross-sectional shape of the cartridge body. On the other hand, it is inventively especially favorable that a relatively minimal deformation of the strand allows the realization of the inventive effect according to which the flow resistance for the high-viscosity material can be minimized. It is especially inventively preferred that no flow resistance obstacles such as thresholds or steps impair the dispensing action of the dental material from the cartridge body. It is especially preferred in this context when the outlet opening is practically a direct extension of the preferably substantially cylindrical cartridge body as regards the cylinder wall which is adjacent to the outlet opening.

Because of the flow-technologically beneficial design for producing the inventive strand, a surface reduction in the ratio of, for example, 1:2.5 between the cross-sectional area of the inner portion of the cartridge body and the outlet opening is possible without generating flow resistances that are too large.

According to a further especially favorable aspect of the invention, the cartridge has no part that is fixedly connected to the cartridge and would laterally project past the circumference of the cartridge. On the contrary, the inventive strand simulates substantially a laterally projecting dispensing socket. This means, on the other hand, that the inventive cartridge, if necessary, can be closed off without problems with a corresponding cover cap (50).

BRIEF DESCRIPTION OF THE DRAWINGS

The object and advantages of the present invention will appear more clearly from the following specification in conjunction with accompanying drawings, in which:

FIG. 4 shows a plan view onto a modified embodiment of the inventive cartridge;

FIG. 5 shows a sectional view of the embodiment according to FIG. 4; and

FIG. 6 shows a side view of the inventive dental applicator.

DESCRIPTION OF PREFERRED EMBODIMENTS

Figure 1:
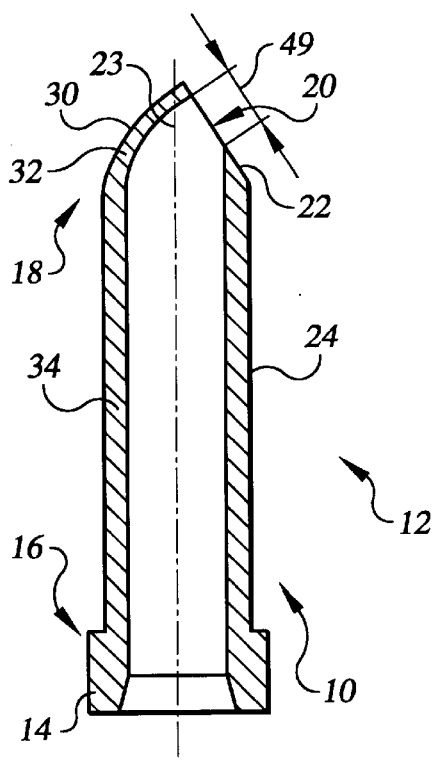
FIG. 1 is a section of one embodiment of the inventive cartridge.

The present invention will now be described in detail with the aid of several specific embodiments utilizing FIGS. 1 through 6. The cartridge 10 which is represented in FIG. 1 has a cartridge body 12 which is substantially cylindrical and which is suitable for receiving a paste-like material. In the cartridge 10 a non-represented plunger is guided by which the paste-like material is dispensed from the cartridge.

Even though the present invention is primarily designed for use with dental materials, it is understood that it can be used instead also with any other paste-like or highly viscous material.

For supporting the pressure forces introduced into the cartridge when dispensing the material, the cartridge body 12 has a support collar 14 which at the rearward end 16 surrounds the cartridge body 12 annularly.

The front end of the cartridge body 12 has an outlet opening 20 via which the material can be dispensed from the cartridge body 12. The outlet opening 20 is embodied within the cartridge body 12 itself, particularly in an outlet wall 22 which extends at a slant to the axis 23 of the cartridge body 12. The normal of the wall surface 22 in the shown embodiment is positioned at an angle of 55° relative to the axis 23 in the forward direction. With respect to the wall 24 of the cartridge body 12, the outlet opening 20 is embodied in the manner of a slanted portion whereby the sectional surface does not extend exactly to the center of the body 12 but ends at a tip 30 of the body 12.

A deflection wall 32 is embodied opposite the outlet opening 20 and curves toward the outlet opening. The deflection wall 32 extends from the wall 34 of the cartridge body 12 positioned opposite the wall 24 toward the axis 23 and intersects the outlet opening wall 22. The deflection wall 32 is preferably curved so that the flow direction of the strand is changed slowly. In this context, it is beneficial when the inner radius of the deflection wall corresponds substantially to the diameter of the cartridge body. In a modified embodiment, it is suggested that the radius increases from the rear to the front so that the deflection of the strand of paste-like material is slow initially and then becomes faster. Inventively, a steady or continuous transition without steps, projections etc. is important in this context so that no flow obstacles are present.

The converging design of the deflection wall 32 in the direction toward the tip causes a cross-sectional narrowing of the outlet opening 20 so that at the same time a nozzle is formed. The cross-sectional narrowing increases slowly so that the flow velocity also increases slowly. The curvature of the deflection wall 32 at its inner side imparts on the exiting strand the tendency to flow in a curved shaped from the outlet opening 20, can be seen in FIG. 2.

In the shown embodiment it is furthermore suggested that the deflecting wall 32 tapers somewhat toward the tip 30 of the cartridge body 12 so that at the tip 30 a substantially reduced wall thickness is provided in comparison to the walls 24 and 34 of the cartridge body 12.

Figure 3:
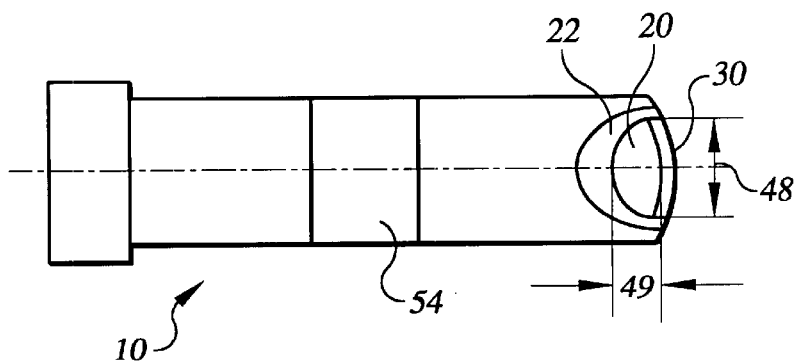
FIG. 3 shows a view of the embodiment according to FIGS. 1 and 2, the view being rotated 90° about the longitudinal axis.

The outlet opening 20 has an asymmetric design with respect to its width and length, as can be seen in detail in FIG. 3. The width is wider at the tip 30. The asymmetric lens-shaped design as shown in FIG. 3 results directly from the realization of the section according to FIG. 1.

Figure 2:
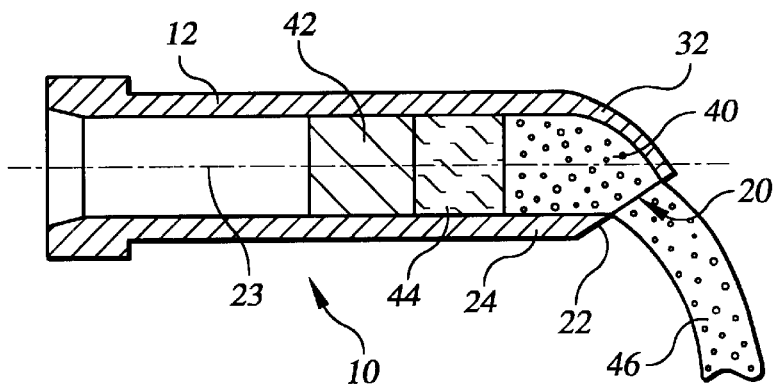
FIG. 2 shows a section of the embodiment according to FIG. 1, whereby the dispensing of viscous dental material is shown.

FIG. 2 illustrates in which manner the dental material 40 is moved out of the cartridge 10. Within the cylindrical cartridge body 12 of the cartridge 10 a piston 42 is guided which moves along the axis 23 until it is stopped by the deflection wall 32. The piston 42 is comprised of a pressure-resistant plastic material and is not considerably deformed by the introduced pressure forces. In the shown embodiment the front end of the piston 42 has a deformation body 44 which upon advancing of the piston 42 is deformed by the deflection wall 32 and upon further movement of the piston 42 fills the entire interior up to the outlet opening 20. With this design it is ensured that no dental material remains within the cartridge body. Even though the dental material, upon complete dispensing from the cartridge body 12, no longer can provide a support function for the dental material strand 46 exiting from the cartridge body 12, at this point in time the deeper areas within the cavity are already completely filled by the dispensed dental material so that this support function is no longer critical.

FIG. 2 shows that the strand 46 projects in a curved fashion from the outlet opening 20. The starting direction of the strand 46 at the outlet opening 20 corresponds substantially to the bisecting line of the inner end area of the deflection wall 32 and the wall 24 adjacent to the outlet opening.

In a modified embodiment it is suggested to provide the piston without a deformation member 44. This solution is suitable for supplying the strand 46 even when the actual dispensing action of the dental material 40 is complete.

FIG. 3 shows a view of the embodiment according to FIGS. 1 and 2, the view being rotated 90° about the longitudinal axis to show the shape of the outlet opening 20. As can be seen, the width 48 of the outlet opening increases toward the tip 30 over a substantial portion of the length 49 of the outlet opening 20 so that its maximum width is reached in the vicinity of the end close to the tip. The axial length 49 of the outlet opening 20 is substantially smaller than the width 48 of the outlet opening 20. In a preferred embodiment it is approximately half the size. The design of the.outlet opening 20 is accordingly substantially trapezoidal or of an asymmetric lens-shape. It is understood that any other suitable design is possible without leaving the principle of the invention. The exiting strand 46 of FIG. 2 adopts exactly the shape of the outlet opening 20 so that the shape of the strand 46 can also be adapted to the specific needs.

FIGS. 4 and 5 show a modified design of the inventive cartridge 10 in which a cap 50 closes off the outlet opening 20. The cap 50 can be placed onto the cartridge when the cartridge 10 is to be reused. It is beneficial that a simple snap-on cap that allows tight sealing is used since no outlet socket is inventively needed. The inventive cartridge can be stored in this manner in a safe fashion without running the risk that the cap will be lost upon handling.

Even though the present invention has been disclosed in the above description with respect to a cartridge, which can be inserted into a cartridge dispensing device, it is understood that instead any other suitable dental applicator can be designed according to the inventive principle.

It is understood that it is possible to provide the cartridge 10 with a labeling field 52 or with colored secured rings 54 which allow an identification of the respective dental material 40 contained in the cartridge.

FIG. 6 shows a dental applicator 56 employing the inventive cartridge as an applicator body. In the shown embodiment a substantially pistol-shaped dental applicator 56 with a slide actuator 58 is represented which releases or secures the cartridge 10 as desired. It is understood that any other suitable dental applicator can be used in the context of the invention, even those that are not pistol-shaped, but instead are of a syringe design.

The present invention is, of course, in no way restricted to the specific disclosure of the specification and drawings, but also encompasses any modifications within the scope of the appended claims.

What is claimed is:

1. A cartridge body for receiving and dispensing a paste-like material with a lateral deflection, said cartridge body comprising:
   a cylindrical portion (24, 34) having a central longitudinal axis (23); and
   a front end portion consisting of two walls (22, 32) converging at a tip (30), which walls do not project laterally past the circumference of the cylindrical portion, one (22) of said two walls defining an outlet wall, the outlet wall (22) having an outlet opening (20) for dispensing the paste-like material, said outlet opening (20) having a width (48) measured in a direction perpendicular to said longitudinal center axis (23), and an axial length (49) measured in a direction of said longitudinal center axis (23), the width (48) of said outlet opening (20) being of greater length than the length (49) of said outlet opening 20), wherein said second converging wall serves as a deflection wall for deflecting the paste-like material into the outlet opening, and wherein said deflection wall curves radially inwardly past said longitudinal center axis.

2. A cartridge dispensing a paste-like material with a lateral deflection, said cartridge comprising:
   a cartridge body (12) provided with a cylindrical portion (24, 34) having a central longitudinal axis (23), and a front end portion consisting of a deflection wall (32) and an outlet wall (22) converging at a tip (30), which walls do not project laterally past the circumference of the cylindrical portion, the outlet wall (22) having an outlet opening (20) for dispensing a paste-like material, said outlet opening (20) having a width (48) measured in a direction perpendicular to said longitudinal center axis (23), and an axial length (49) measured in a direction of said longitudinal center axis (23), the width (48) of said outlet opening (20) being of greater length than the length (49) of said outlet opening 20);
   a paste-like material (40) disposed within said cartridge body (12); and
   a plunger (42, 44) slidably guided in said cartridge body (12), which plunger may be moved towards the tip for dispensing the paste-like material, said deflection wall serving as a stop for said plunger.

3. A cartridge according to claim 2, wherein said plunger has a deformable displacement member and wherein said plunger is mounted in said cartridge body such that said deform able displacement member faces said outlet opening.

* * * * *